United States Patent [19]
Stetter et al.

[11] Patent Number: 5,448,905
[45] Date of Patent: Sep. 12, 1995

[54] SOLID-STATE CHEMICAL SENSOR APPARATUS AND METHODS

[75] Inventors: Joseph R. Stetter; William J. Buttner, both of Naperville, Ill.

[73] Assignee: Transducer Research, Inc., Naperville, Ill.

[21] Appl. No.: 157,529

[22] Filed: Nov. 26, 1993

[51] Int. Cl.⁶ .................... H01C 7/00; G01N 27/04
[52] U.S. Cl. ................... 73/31.05; 73/23.21; 73/28.01
[58] Field of Search .......... 73/31.05, 31.06, 23.21, 73/28.01

[56] References Cited

U.S. PATENT DOCUMENTS

| | | | |
|---|---|---|---|
| 3,676,820 | 7/1972 | Taguchi | 338/34 |
| 3,739,260 | 6/1973 | Schadler | 324/33 |
| 3,751,968 | 8/1973 | Loh et al. | 73/31.05 |
| 3,945,244 | 3/1976 | Wormser et al. | 73/40.7 |
| 3,952,567 | 4/1976 | Shinagawa et al. | 73/31.05 |
| 3,991,360 | 11/1976 | Orth et al. | 324/33 |
| 4,224,280 | 9/1980 | Takahama et al. | 422/98 |
| 4,587,104 | 5/1986 | Yannopoulos | 422/94 |
| 4,601,883 | 7/1986 | Sekido et al. | 422/94 |
| 4,609,875 | 9/1986 | Jeffers | 324/455 |
| 4,627,269 | 12/1986 | Forster et al. | 73/23 |
| 4,663,958 | 5/1987 | Matthiessen | 73/1 G |
| 4,674,320 | 6/1987 | Hirschfeld | 73/23 |
| 4,675,030 | 6/1987 | Czarnecki et al. | 55/16 |
| 4,701,187 | 10/1987 | Choe et al. | 55/16 |
| 4,717,407 | 1/1988 | Choe et al. | 62/18 |
| 4,730,478 | 3/1988 | Gedeon | 73/23 |
| 4,854,155 | 8/1989 | Poli | 73/27 R |
| 4,911,892 | 3/1990 | Grace et al. | 422/94 |
| 4,984,450 | 1/1991 | Burger | 73/40.7 |
| 5,218,347 | 6/1993 | Deppe | 340/634 |
| 5,224,350 | 7/1993 | Mehra | 62/17 |
| 5,226,309 | 7/1993 | Stetter et al. | 73/31.06 |
| 5,284,569 | 2/1994 | Lee et al. | 204/425 |

OTHER PUBLICATIONS

Umezu et al, "New Automatic Leak Testing System With Helium Mass Spectrometer Leak Detector", Journal of Vacuum Society of Japan, vol. 17, No. 2, 1974, pp. 45-52.

Primary Examiner—Hezron E. Williams
Assistant Examiner—J. David Wiggins
Attorney, Agent, or Firm—Solomon Zaromb

[57] ABSTRACT

In solid-state chemical sensors, such as the highly sensitive and selective sensor for the detection of halogenated compounds comprises a bead of sodium lanthanum fluoride silicate, having the molecular formula $NaLa_4(SiO_4)_3F$, the performance and lifetime are adversely affected by a build-up of insulating reaction product between two electrodes. To prolong the lifetime, intermittent sensor operation is achieved by applying a voltage between the sensor electrodes during only a small fraction of each measurement cycle and/or by reversing the voltage in successive measurement intervals and/or by switching the connections between additional reserve electrodes and/or by periodically exposing the sensor to chemically filtered air at regular time intervals during a major fraction of each measurement cycle. The response speed and sensitivity of the $NaLa_4(SiO_4)_3F$ sensor are improved when platinum black is interspersed with or otherwise added to the bead material during the preparation of the sensor. Improved reproducibility and additional sensing capabilities are also achieved by means of a feedback circuit that assures automated temperature constancy of the sensor bead and, at the same time, permits simultaneous estimation of the concentration of both halogen-containing and halogen-free combustible compounds. Provisions for a jump in the sensor temperature and for exposing the sensor to halogen-depleted air at the end of each measurement cycle minimize the effects of baseline drift and thereby yield higher sensitivity and measurement accuracy.

34 Claims, 7 Drawing Sheets

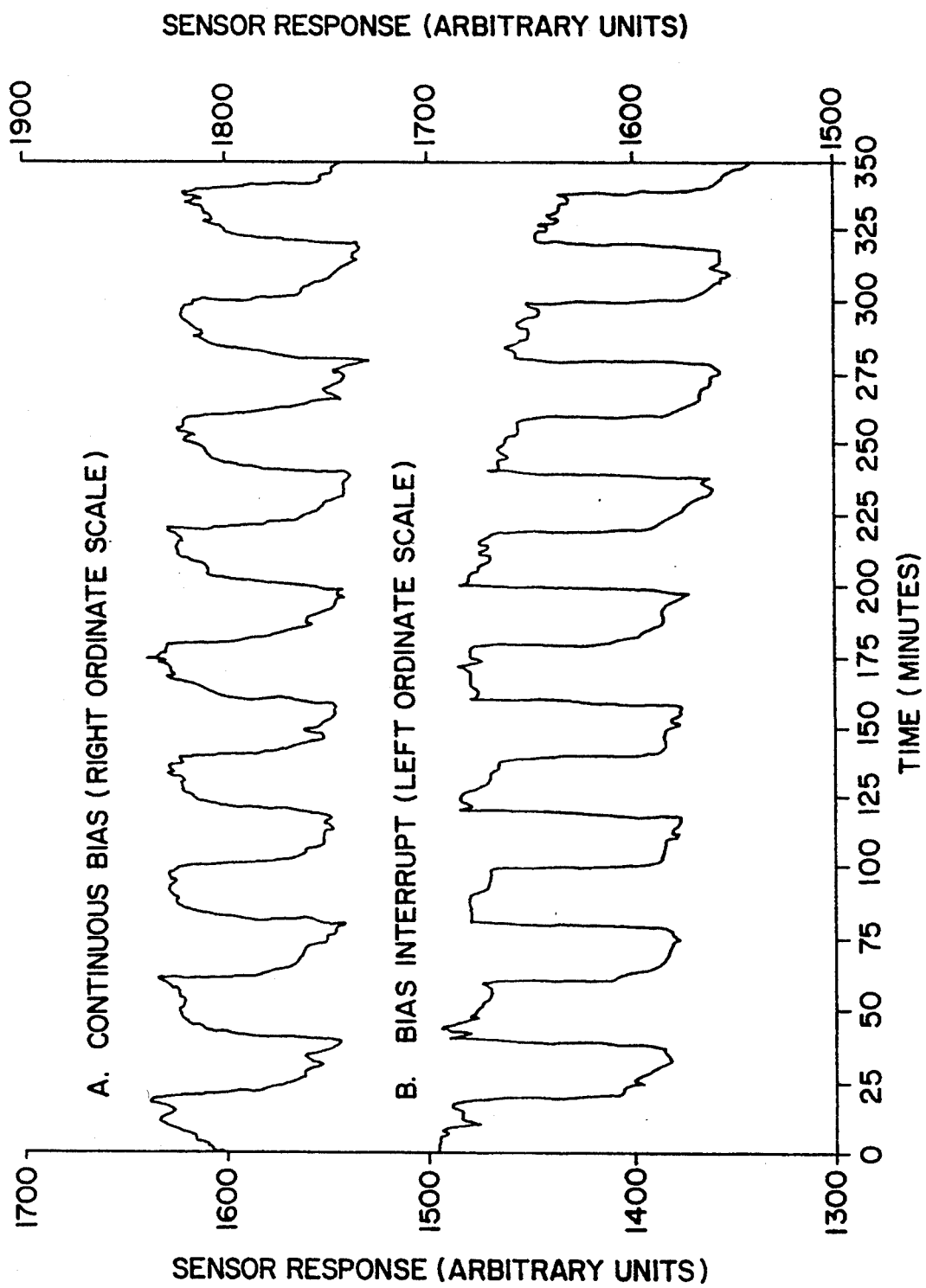

SOLID-STATE CHEMICAL SENSOR APPARATUS AND METHODS

BACKGROUND OF THE INVENTION

This invention relates to improvements in apparatus and methods for the detection of chemical substances, and especially of halogenated compounds, such as chloropentafluorobenzene, chlorobenzene, trichloroethylene, dichloromethane, chloroform, chloroethyl ethyl sulfide, dichloro-diethyl sulfide, hydrogen chloride [HCl], bromobenzene, bromopropane, iodobenzene or iodopropane, all of which, except HCl, have a carbon-halogen chemical bond.

Many halogenated compounds, especially chlorinated hydrocarbons, are believed to be harmful to the environment and human health either through direct exposure (potential carcinogenicity) or indirectly through their adverse effect on the ultraviolet-absorbing stratospheric ozone layer. Sixteen chlorinated hydrocarbons are among the 25 organic compounds that were recently added by the Environmental Protection Agency to the list of chemicals that are to be regulated as toxic wastes under the Resource Conservation and Recovery Act. Rules have also been issued for a 50% reduction in the production and importation of chlorofluorocarbons by the year 1995.

It is an object of this invention to provide a sensor that is relatively inexpensive and portable and that can reliably and selectively detect various halogenated compounds. To achieve the required controls, it will be necessary to resort to relatively inexpensive yet well-functioning halogenated compound monitors.

Of the few sensors that have been developed for the detection of halogenated compounds, each has serious shortcomings. A chlorinated hydrocarbon gas sensor consisting of a ZnO-based semiconductor with vanadium, molybdenum and alumina catalysts was reported by M. Shiratori, M. Katsura, and T. Tsuchiya in the *Proceedings of the International Meeting on Chemical Sensors*, Fukuoka, Japan, T. Seiyama et al., editors (Elsevier, N.Y., 1983), pp. 119–124. Another sensor system responsive to chlorinated hydrocarbons was reported by J. Unwin and P. T. Walsh in *Sensors and Actuators*, 18:45 (1989). This system decomposes the chlorinated compounds over a heated platinum coil and measures the changes in the electrical conductivity of a lead phthalocyanine film that is exposed to the decomposition products. Even earlier, Stetter et al. (*Sensors and Actuators*, 6:269–288 (1984)) reported the detection of such compounds by room-temperature electrochemical (amperometric) sensors following exposure to a heated noble-metal filament. Commercially available photoionization detectors also exist that respond to halogen compounds. The problem with all of these sensing systems is that they are non-selective and will respond to certain halogen-free compounds, such as methane, ethanol, benzene, hexane or nitrogen dioxide. Also, many of the prior techniques lack the sensitivity that is needed. There are also gas chromatographic detectors for chlorinated hydrocarbons that are based on Hall conductivity or electron capture. However, these systems are complex, expensive, and sensitive to interferences. In addition, they can be large, not environmentally rugged, or not sufficiently sensitive (the action level for $CCl_4$ is often 1 ppm [part per million by volume]).

It is therefore another object of this invention to provide a sensor and method that is relatively simple, inexpensive, and that can selectively detect halogenated compounds in the presence of potentially interfering substances with high sensitivity and in a rugged solid state design.

A solid-state sensor, disclosed by J. C. Loh and C. Lu in U.S. Pat. No. 3,751,968, dated Aug. 14, 1973, was claimed to be capable of detecting dichlorodifluoromethane in a concentration as low as 20 ppb (parts per billion by volume). The stone sensor was also intended for the detection of other chlorofluorocarbons, as well as of sulfur hexafluoride, chloroform, and carbon tetrachloride. This sensor is formed of a glass-ceramic mixture of sodium or lithium silicate, lanthanum oxide, and lanthanum fluoride in a preferred molar ratio of $[La_2O_3]_{(1-2)}[LaF_3]_{(3-4.5)}Na_2SiO_3$. The preparation of this sensor involves the formation of a surface depletion layer through application of "a biasing D.C. voltage of 1–10 volts" at a temperature above 500° C., preferably 600° C., for about 24–48 hours. No information is disclosed in the patent about the performance of this sensor. However, in view of the wide range of preferred molar ratios, one would expect the performance to vary widely from unit to unit.

U.S. Pat. No. 5,226,301, dated Jul. 13, 1993, a sensor is disclosed by J. R. Stetter and Z. Cao that bears some resemblance to that of U.S. Pat. No. 3,751,968 but overcomes the above-cited disadvantages of the earlier sensor. The newer sensor consists of a bead of sodium lanthanum fluoride silicate, having the molecular formula $NaLa_4(SiO_4)_3F$, as determined by x-ray (diffraction) crystallography, in which are embedded two noble metal electrodes, preferably a straight platinum wire near the center and a helical platinum wire near the periphery of the bead. A current passing through the helical wire maintains the sensor temperature at about 550° C. by resistive heating. The electrical resistance between the two wires is deduced from measurements of the current passing through a fixed external resistor mounted in series with one electrode when a substantially constant voltage, typically about 3 volts, is applied between the wires. An increase in the measured current (at constant voltage) is an indication of the presence of a halogenated compound in the sample of air to which the bead is exposed. The sensor is preferably controlled by a micro-processor or microcomputer that also performs data processing. This system not only detects a halogenated compound of interest, but also measures its concentration. The lifetime is limited by the history of exposure. Continuous exposure to chlorinated vapors (ca: 10 ppm) can limit lifetime. Also, performance may be limited for applications where fast response and long lifetime are needed.

It is therefore still another object of this invention to provide a sensor having an extended lifetime and that has well-defined, improved, and reproducible performance characteristics.

The lifetime limitation appears to arise from a build-up of an insulating substance between two sensor electrodes. A similar build-up may adversely affect the performance and lifetime of other solid-state sensors. It is therefore an object of this invention to provide apparatus and methods for improving the performance and lifetime of any solid-state sensors that may be adversely affected by a build-up of an objectionable chemical reaction product resulting from operation and exposure of the sensor to a monitored analyte.

Other objects of the invention will become obvious to professionals in various fields, such as industrial hygiene, medical monitoring, process control, military, aerospace, or pollution monitoring, following perusal of the complete specification.

SUMMARY OF THE INVENTION

Briefly, this invention addresses the cause of the limited lifetime, which may be due to a build-up of an insulating layer between two sensor electrodes. In the halogenated compounds sensor, the insulating layer is formed as a result of exposure to halogenated compounds and its build-up increases with the time and level of exposure to such compounds during operation. This build-up can be slowed down by intermittent sensor operation. This can be achieved by applying a bias voltage between the sensor electrodes during only a small fraction of each measurement cycle and/or reversing the bias in successive measurement intervals and/or by periodically exposing the sensor to chemically filtered air at regular time intervals during a major fraction of each measurement cycle. Alternatively, or in addition, the sensor lifetime can be further extended by switching the connections between additional reserve electrodes formed in the sensor during fabrication so as to divert the objectionable build-up to a new unobstructed portion of the sensor bead. Additional reserve electrodes may be incorporated into the bead and switched on during successive measurement cycles or when the first pair of electrodes is used up.

It has also been found that the sensor can be made faster responding and exhibiting higher sensitivity when platinum black is interspersed with or otherwise added to the bead material during the preparation of the sensor. Improved reproducibility and additional sensing capabilities are also achieved by means of a feedback circuit that assures automated temperature constancy of the sensor bead and, at the same time, permits simultaneous estimation of the concentration of both halogen-containing and halogen-free combustible compounds. Further improvements include provisions for a jump in the sensor temperature and for exposing the sensor to halogen-depleted air at the end of each measurement cycle in order to minimize the effects of baseline drift and thereby yield higher sensitivity and measurement accuracy.

BRIEF DESCRIPTION OF THE DRAWINGS

The invention is best explained with reference to the drawings, in which:

FIG. 4 shows the response of a sensor to 20 ppm of carbon tetrachloride when operated with continuous bias [FIG. 4A] and with cyclic interruptions of the bias voltage;

DESCRIPTION OF THE PREFERRED EMBODIMENTS

Ancillary Components

Figure 1A:
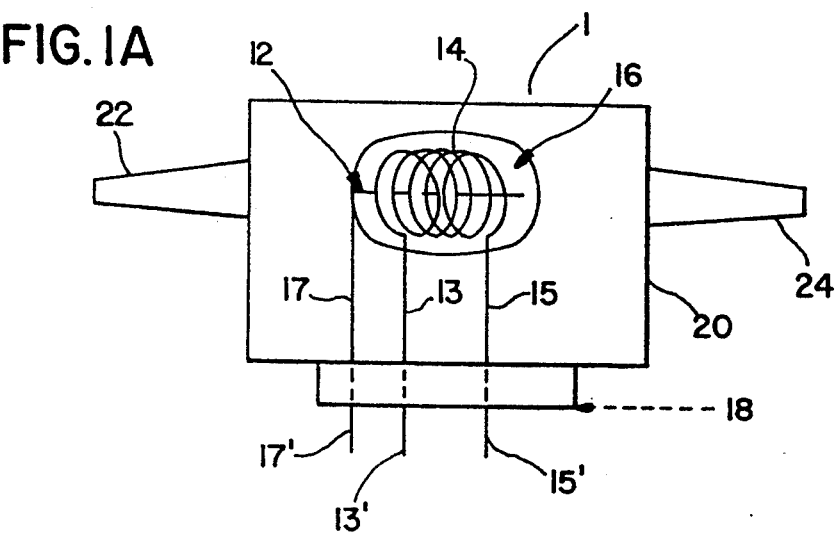
FIG. 1A is a schematic diagram of the main components of one embodiment of the invention and of the sensor of the copending application Ser. No. 07/900,916.

FIG. 1A is a schematic diagram of one embodiment of the sensor 1 of this invention or of the afore-mentioned copending application Ser. No. 07/900,916, which comprises a platinum wire 12 surrounded by a platinum coil 14, both embedded in a bead 16 that is composed mainly of $NaLa_4(SiO_4)_3F$. The two ends 13 and 15 of coil 14 and one end 17 of wire 12 are connected to pins 13', 15', and 17', respectively, of a miniature socket 18 comprising four or more pins. As shown in the schematic diagram of FIG. 1B, an alternative embodiment of the sensor of this invention comprises additional wires 12*, 12**, ... with ends 17*, 17**, ... connected to pins 17*', 17**' ... Also, in FIG. 1C, are shown additional wires 19, 19* in different locations on the sensor bead 16, as well as pins 19', 19*', to measure the sensor's current-voltage characteristics. Bead 16 is enclosed within a chamber 20 comprising an air inlet 22 and an air outlet 24. Chamber 20 is preferably made of an electrically conductive material, such as aluminum, to provide electrical shielding, and should be covered by a thermally insulating material [not shown] to provide thermal shielding.

To form bead 16, coil 14 is first prepared by winding six to twelve turns of a platinum wire, typically about 0.1 mm in diameter, around a 1.5-mm-diameter rod, so as to produce a coil length of about 2.5 mm, sliding the coil off the rod, and mounting the two ends of the coil 13 and 15 onto socket 18. The nature and size of the heater is chosen to be compatible with bead forming and desired electrical heating and power characteristics. Next, lanthanum oxide ($La_2O_3$) and lanthanum fluoride ($LaF_3$) powders are mixed with an aqueous solution of sodium silicate ($Na_2SiO_3$) to form a paste. The three components of the paste are preferably in a molar ratio corresponding to the chemical formula $La_2O_3.2LaF_3.3Na_2SiO_3$. End portions of wires 12, 12*, 12**, ... are then coated with the paste and dried by heating. The coated wires are fitted axially into the coil, and additional paste is applied so as to cover the coil. Air drying of the materials is also possible prior to sintering. The bead is finally formed by gradual raising of the temperature of the heating coil followed by sintering at about 800° C. for 3–8 hours.

The shape of the formed bead is determined by the amount of paste added to cover the coil and wires and by the configuration and vertical orientation of the coil and wires during the sintering step. Preferred shapes of bead 16 may be obtained by techniques that are well known in the arts of mechanical engineering, chemistry, microfabrication, electronics, materials science, pottery and ceramics.

Figure 2:
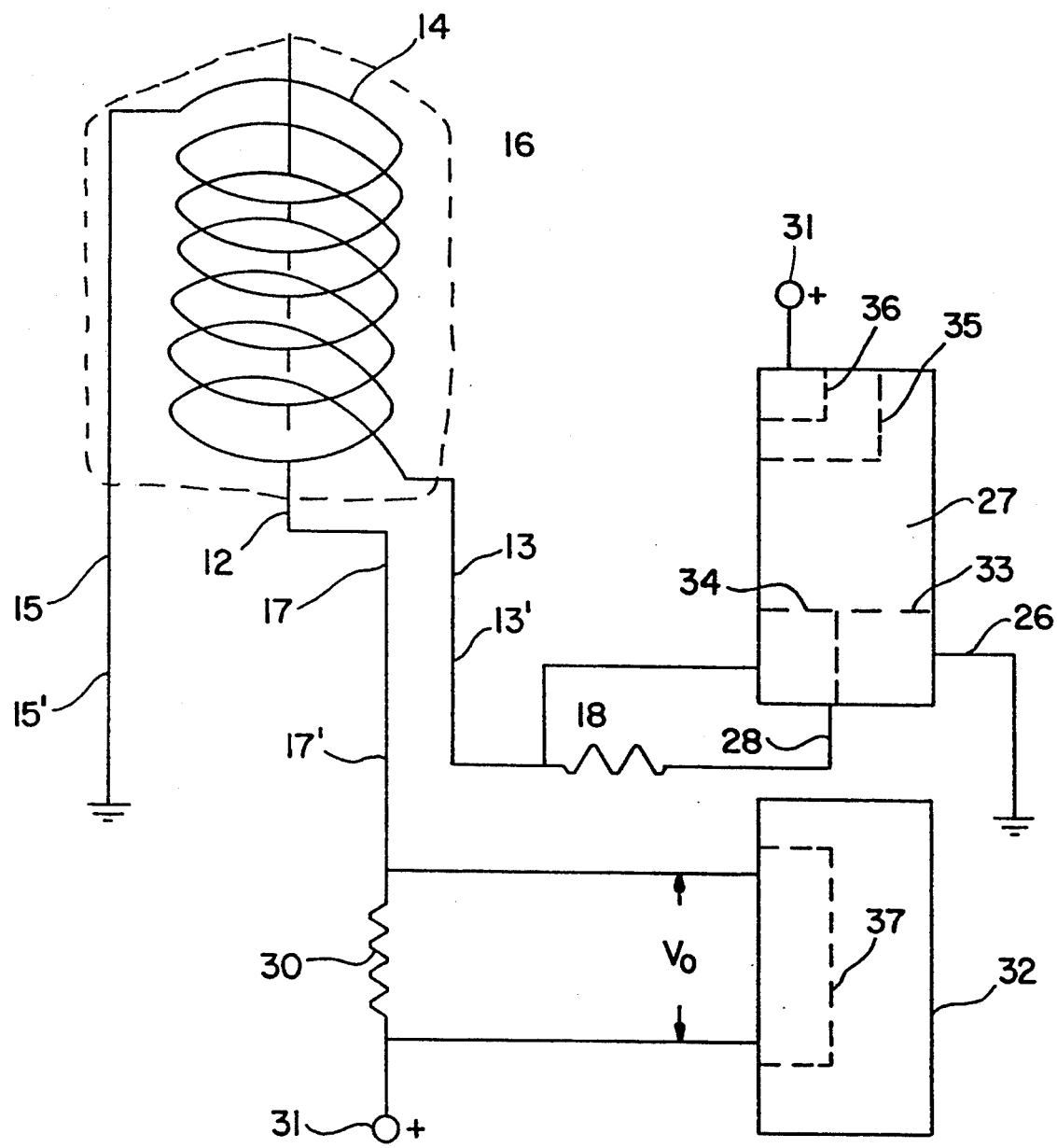
FIG. 2 shows one type of basic electrical circuit that is required for the operation of the sensor.

To be operational, the sensor must form part of the electric circuit of FIG. 2, in which:

pin 15' is connected through the ground to one output terminal 26 of a heater power supply 27.

pin 13' is connected via resistor 18 to a second voltage terminal 28 of heater power supply 27; and pin 17' [or 17*' or 17**' or 19' or 19*' or the like] is connected to one end of a resistor 30, which is connected at its other end to the positive terminal 31 of the power supply 27.

The current i that flows through resistor 30, wire 12 [or 12* or 12** or 19 or 19* or the like], and bead 16 is then determined by measuring the voltage drop $V_o$ across resistor 30 using an appropriate device 32, which may be a simple voltmeter, a recorder or a signal amplifier and microprocessor circuit. The sensor temperature is raised to a preferred value, usually 550° to 800° C., typically by resistive heating of coil 14. The current in coil 14 is determined by measuring the voltage drop across resistor 181. The voltage applied to coil 14 is regulated to maintain a constant operating condition [e.g., temperature or input power]. This yields a sensor output that is not affected by line-voltage variations, shortens the warm-up time of cold sensors, and minimizes sensor output drift.

Figure 3:
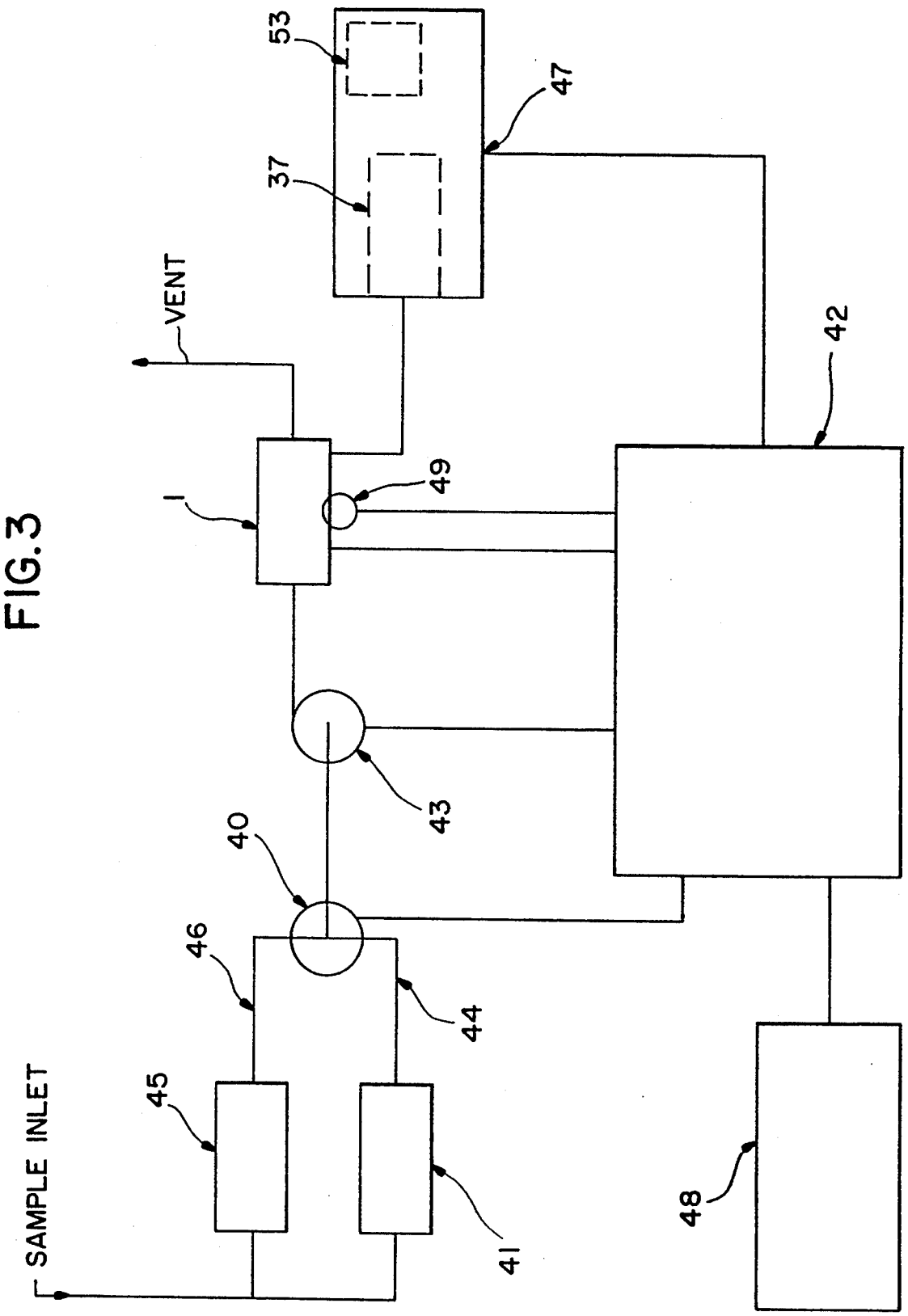
FIG. 3 is a block diagram of a complete monitoring system incorporating the sensor and circuitry of FIGS. 1 and 2.

Making use of the known temperature coefficient of the electrical resistivity of platinum, the temperature of coil 14, and hence of the sensor bead 16, can be controlled by a suitable circuit means similar to that disclosed in FIG. 3 of the copending application Ser. No. 07/900,916, which is included herein by reference. The voltage across coil 14 is measured and fed into a comparator circuit 33 held at fixed voltage. The output of the comparator 33 is damped to prevent oscillation.

The temperature of the sensor can be monitored by recording the current and voltage across coil 14 with an appropriate device, such as the microprocessor 42 of FIG. 3. Since a microprocessor only records a voltage signal, a current-to-voltage converter 34 is used to transform the heater current into a voltage signal. Other approaches to controlling and measuring the electrical operating and measuring parameters can be readily applied by persons skilled in the art.

The sensor bias voltage [i.e., the potential of terminal 31 relative to ground] is preset by an adjustable voltage follower 35 and is adjustable with a potentiometer 36. Since the actual current between the two electrodes 12 and 14 of the sensor is very low, a buffered differential amplifier circuit 37 followed by a second stage amplifier [not shown] can be used to convert the current through the sensor into an amplified voltage signal. This amplifier circuit can be interfaced with the microcomputer 42 for data logging and processing. Of course, there are many more buffering, filtering, controlling and amplifying circuits that can be used to make an entire instrument system.

A block diagram of a complete instrument system for monitoring halogenated hydrocarbon vapors is shown in FIG. 3. A solenoid valve 40 controlled by a microcomputer 42 opens one of two inlets 44 and 46 which admit either pure air, also referred to as "zero air" [through a "zero" filter 41] or the gaseous sample [after removal of interferences by a selective chemical filter 45] into a flow system that includes a chlorinated hydrocarbon (RCl) vapor sensor 1, and an air pump 43. The zero filter 41 comprises a suitable adsorbent, such as activated charcoal, which removes RCl vapors from the gaseous sample. By switching valve 40, it is possible to rapidly change the flow through sensor 1 over the sensor bead 16 from that of RCl-depleted air to that of sampled air. The flow is preferably maintained constant at about 350 mL/minute by mechanical means, such as a battery-powered air pump. A programmed measurement cycle preferably includes sample exposure for 5 minutes followed by clean air exposure for 5–10 minutes. This has the effects of reducing total exposure to halogenated compounds, thereby extending the life of the sensor [see the following paragraph], and of providing a better defined "zero" baseline, thereby improving the sensitivity and the accuracy of the measurements. Also, this pneumatic arrangement can be used to provide an automatic dilution of the sample that can be used to limit exposure levels to lengthen sensor lifetime, or to extend the dynamic range of the sensor. The signals from the RCl sensor are transferred by a circuit 47, also referred to as "RCl driver," to the microcomputer 42. Also transferred to the microcomputer 42 by the amplifier 37 and a temperature monitor 49 are the changes in the current-voltage characteristics (conductance) of bead 16, also referred to as "sensor signals," as well as the voltage across and current through coil 14. The microcomputer 42 serves to record the sensor signals, to control valve 40 and a display 48, and to store the collected data in its memory. The RCl driver 47, comprising the circuits 27 and 32 of FIG. 2, may be used in conjunction with microcomputer 42 to adjust the sensor temperature and other test conditions, such as the operation of valve 40 or the gas flow rate through sensor 1.

Bias-Interrupt Operation

One of the limitations of the sensor of application Ser. No. 07/900,916 is the relatively short lifetime. Prior work indicates that the major failure mode is a function of the total exposure and may include formation of an insulating layer at one of the polarized electrodes. Device failure is often observed as a lack of conductance. One solution to this problem is to turn on the device bias only when a reading is required. One embodiment of this invention is to include in the microcomputer 42 or the RCl driver 47 a bias-interrupt means 51 which programs measurements to be performed with a sensor bias that is "on" for only a fraction of the time, e.g., for only 10 of every 100 seconds [10% duty cycle]. Measurement of sensor conductance nine seconds after bias connection gives a response that is similar to the continuous bias results and proportional to concentration (the sensor bias is turned off for 90 seconds after the 10-seconds-on period). With a 10% bias duty cycle, the buildup of an insulating layer is 10 times slower and thus the sensor lifetime is significantly extended. The effect of the bias-interrupt feature is demonstrated in FIG. 4, which shows sensor response to repetitive exposures each of 10 minutes' duration to 20 ppm carbon tetrachloride and to clean air. The sensor response for continuous bias is illustrated (FIG. 4A) relative to a 10%-bias-on [10 seconds on, 90 seconds off] cycle (FIG. 4B). The net operational time [and hence effective exposure time] for the sensor in FIG. 4B [with the sensor output being monitored only during each 10-second bias-on period] is 10% of that in FIG. 4A. FIG. 4 shows that use of the bias-interrupt method does not degrade sensor performance. Also, it will be clear to those skilled in the art that many different bias-interrupt methods with a variety of time on/off cycles may be used to extend or shorten lifetime in different applications.

Multidimensional Sensing Methods

Figure 5A:
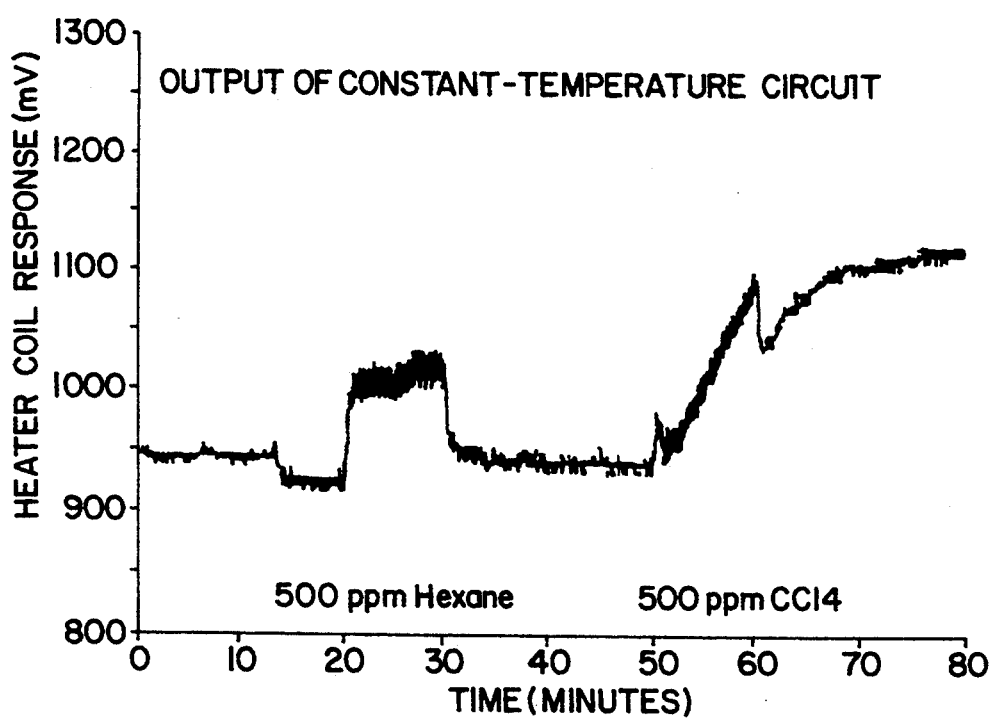
FIG. 5 shows the outputs of a variant of the circuit of FIG. 3 upon exposure of the sensor first to 500 ppm of hexane and next to 500 ppm of carbon tetrachloride.
Figure 5B:
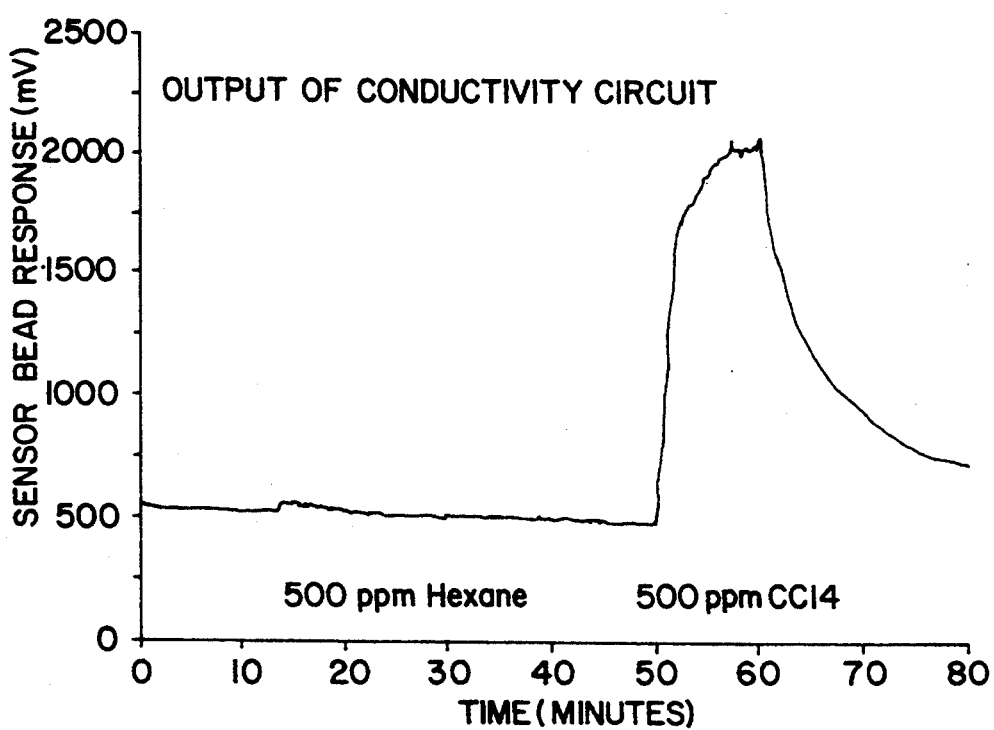

Since the sensor is hot and capable of dissociating chlorinated hydrocarbons, it can be also used to dissociate all hydrocarbons. To test this possibility, the RCl driver 47 of FIG. 3 was provided with a circuit means 53 which has the additional capability to keep the sensor operation at constant resistance of the sensor coil and simultaneously to measure the power required to operate the sensor bead. This means that if the gas heats the sensor, less power will be required to keep it hot. This lower power requirement can be used as a signal that a heating or burning gas is present. This is a principle used in some commercial combustible gas sensors which comprise a noble metal as the primary sensing element. Circuit means 53 comprises a constant-temperature [constant-resistance] control circuit of the kind used to operate commercial combustible gas sensors. As shown in FIG. 5, such a dual circuit is capable of detecting combustible gases [hexane at 500 ppm by measuring the power requirements of the sensor using the combustible gas detection circuit] while at the same time detecting chlorinated hydrocarbons [using the conductance means, because of the biased electrodes and the current and voltage detection circuit already in place in the sensor bead]. FIG. 5 illustrates the selectivity of this dual circuit. The same sensor bead was exposed to 500 ppm of both hexane and carbon tetrachloride. The RCl-detection circuit does not respond to hexane, whereas the constant-temperature circuit does. It is less noteworthy that the latter circuit also yields some response to carbon tetrachloride, since the combustible gas sensor does not distinguish very well between different hydrocarbons. But, it is exceedingly important and surprising to get a well-behaved combustible gas sensor response from an RCl bead with its composition being very different from heretofore known combustible gas sensors.

This multidimensional sensing is a very new sensing procedure for a chemical sensor when applied to this device, and surprisingly good [accurate, sensitive, selective, fast-response, low-cost] measurement capability is achieved. It is unexpected that a bead of rare earth oxides and fluorides would produce a combustibles detection capability of such high sensitivity and this type of material has never before been used for this purpose.

Frequently, multiple classes of vapors exist in an area, and it could be very important that both of these measurements be made simultaneously in environmental applications. With multidimensional analyses, a single sensor could replace two or more instruments and yield sensors offering cost savings and convenience to the user. Further, additional selectivity is obtained because well behaved combustible gas signals and RCl signals are both elicited only from a reduced subset of chemicals!

Sensor Formula Improvements

One of the limitations of the present sensor is a relatively slow response time and recovery time. Improvements here decrease the time per analysis and increase the number of applications that are possible, such as in real-time monitoring and in detectors for gas chromatographs.

Figure 6A:
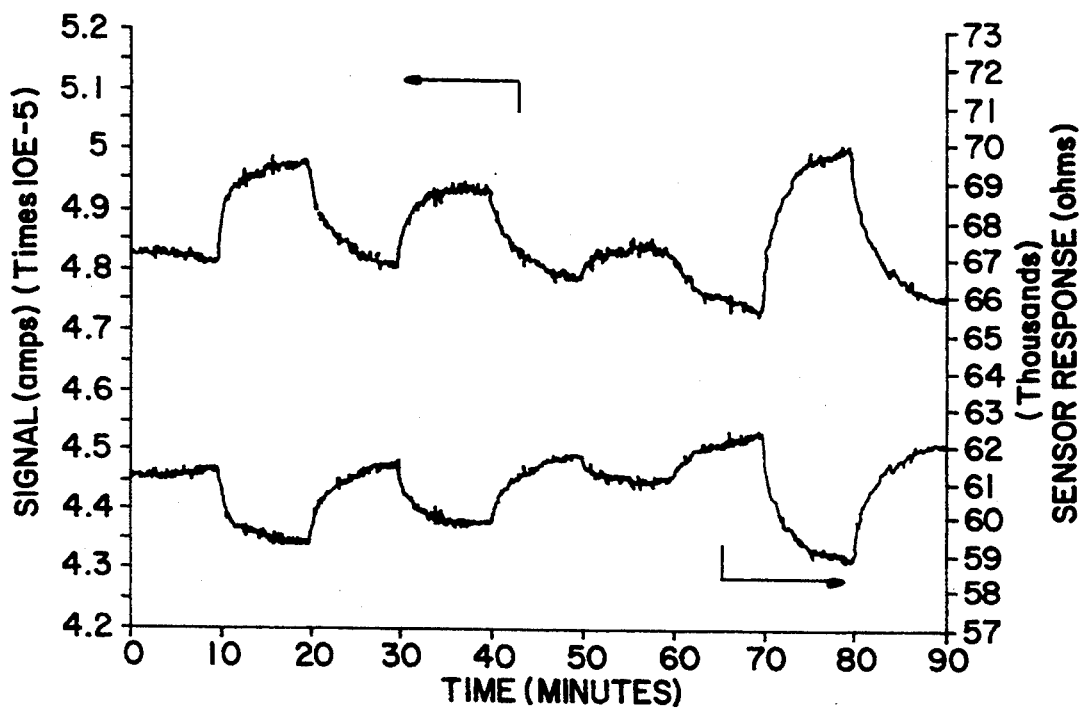
FIG. 6 shows the responses of two sensors of differing composition to several different concentrations of carbon tetrachloride.
Figure 6B:
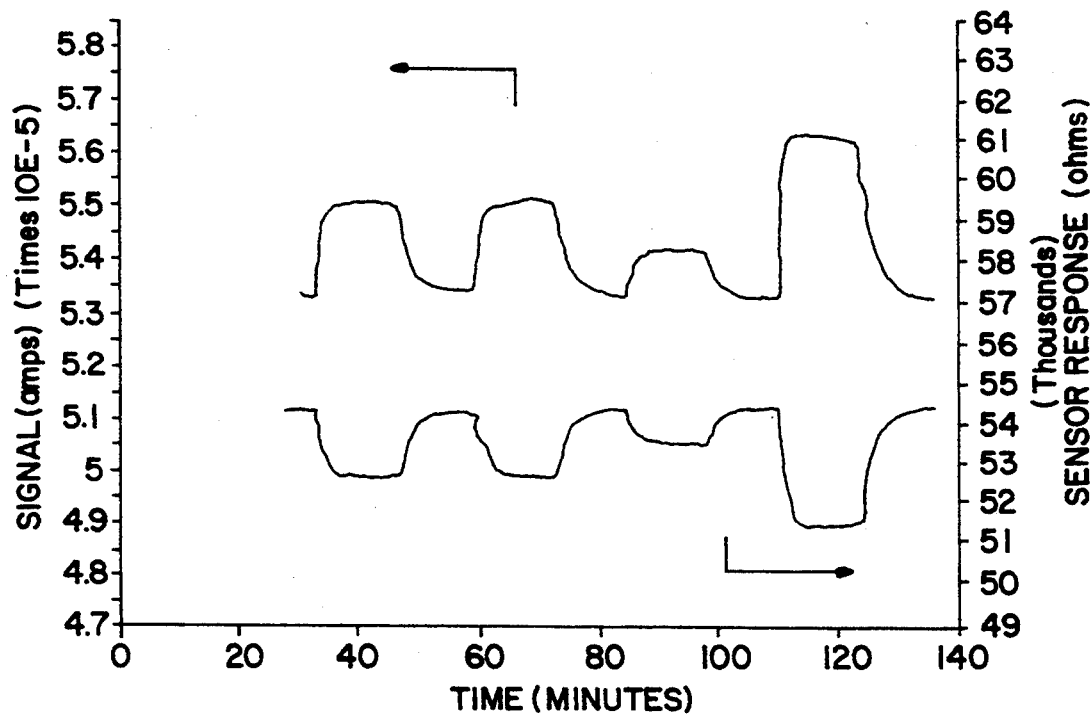

In another embodiment of the invention, the sensor bead is impregnated with 0.1% to 10% by volume of a catalyst [Pt black particles] during preparation. This sensor exhibits a much improved response time and an even better signal magnitude. FIG. 6 shows a comparison of the responses obtained with two otherwise identical sensors, one of which contained an interspersed platinum black catalyst in the sensor bead. Both sensors were exposed for 10-minute periods to $CCl_4$ concentrations of 10 ppm, 10 ppm, 5 ppm and 20 ppm. The improvement achieved through impregnation of the bead with a catalyst was an unexpected finding because increasing the activity of the surface could lead to oxidation of the responding species instead of formation of the detectable RCl derivative! Also it is not obvious that such a change in composition would not degrade other operating parameters.

The improvements observed with the interspersed Pt black may be due to either a catalytic effect or to the formation of multiple electrically conducting bridges that provide alternative current paths around the portions of the bead that are obstructed by the afore-discussed built up insulating layer. Therefore, the interspersed Pt black may also be expected to extend the life of the sensor. For the same reason interspersed non-catalytic conductive particles, including metals, semiconductors or ionic conductors, such as Cu, Ni, iron, graphite, silicon $SnO_2$, ZnO, or silver iodide, may also be expected to yield some of the improvements that are observed with Pt black. It is expected that the inclusion of a catalyst in the bead composition will also improve the afore-disclosed multi-gas sensing capability of the single bead.

Although the results of FIG. 6 were obtained with a bead in which the Pt black catalyst was approximately uniformly interspersed, it is expected that inclusion of the catalyst only in the outer layers of the bead may have similar beneficial effects. As is typical with catalysts, the structure (surface area and nature and size of pores) is critical to effective use. Therefore, for each formula for 0% to x % additive, the porous nature of the bead must be optimized in order to achieve optimum dispersion and activity of the additive and optimum mass transport or kinetics for the rise and decay portions of the sensor response curve. Similarly, an optimized bead geometry, e.g., a thin, disk-shaped structure, may permit faster response and recovery times of the sensor.

It is apparent now that a catalyst region within or near the surface of the bead can controllably serve to promote formation of the most readily detectable species. Therefore, inclusion of various types of active catalyst regions by admixture, deposition, or other types of additions can be resorted to. As shown in FIG. 6, Pt black is very effective in improving the response time and the sensor signal. Other noble metals such as Pd, Ag, Au, and the like, as well as oxide catalysts [$SnO_2$, NiO] and transition metal catalysts [Mo, Ni, Cu—Ni] and their alloys, may be similarly effective. Porous and thin structures may lead to optimum configurations for maximum activity of additives and kinetics of reactions and mass transport.

Autozero and Related Options

The circuit of FIG. 3 has been used most effectively to provide a so-called "autozero" function that corrects for background drift and thereby yields more accurate measurements. Sample vapors are exposed to the sensor and the response of the sensor is recorded by the microcomputer 42. After the analytical cycle, which is typically 10 minutes but can be adjusted to any desired length, the microcomputer 42 activates the solenoid valve 40, which then passes the sample vapor through the zero filter 41, which removes all chlorinated vapors from the sample vapor and to the sensor. Since no reactive vapors are present in the air stream, the sensor output recovers to the baseline. The baseline level is measured and stored in the memory of microcomputer 42. The automated background measurement is called "Autozero." The baseline responses of all chemical sensors are plagued with long term drift which occurs on the time scale from minutes to days, and this drift is unpredictable and frequently large. If uncorrected, the sensitivity of a sensor is frequently limited by the magnitude of this long term drift. Thus the autozero feature significantly improves the sensitivity of the sensor, as well as its accuracy.

A similar system can be programmed to reduce the exposure of the sensor bead during each measurement cycle by alternating the flows of the sampled gas and of pure air past the sensor bead so as to expose the bead to chlorinated hydrocarbons during only a fraction of the cycle. This should operate similarly to the bias-interrupt feature in lengthening the lifetime of the sensor bead.

Temperature Jump

Recovery of the sensor following exposure to vapors of RCl is slow and can take up to 2 hours for field recovery. The recovery kinetics ultimately limits the frequency of measurements. The recovery kinetics is actually complex and multiphasic. Recovery can depend upon bead size and structure (e.g. porosity) as well as the history (level and time) of exposure. However, the slow, rate limiting phase can often be accelerated significantly by adjustment of the sensor operating temperature.

Figure 7:
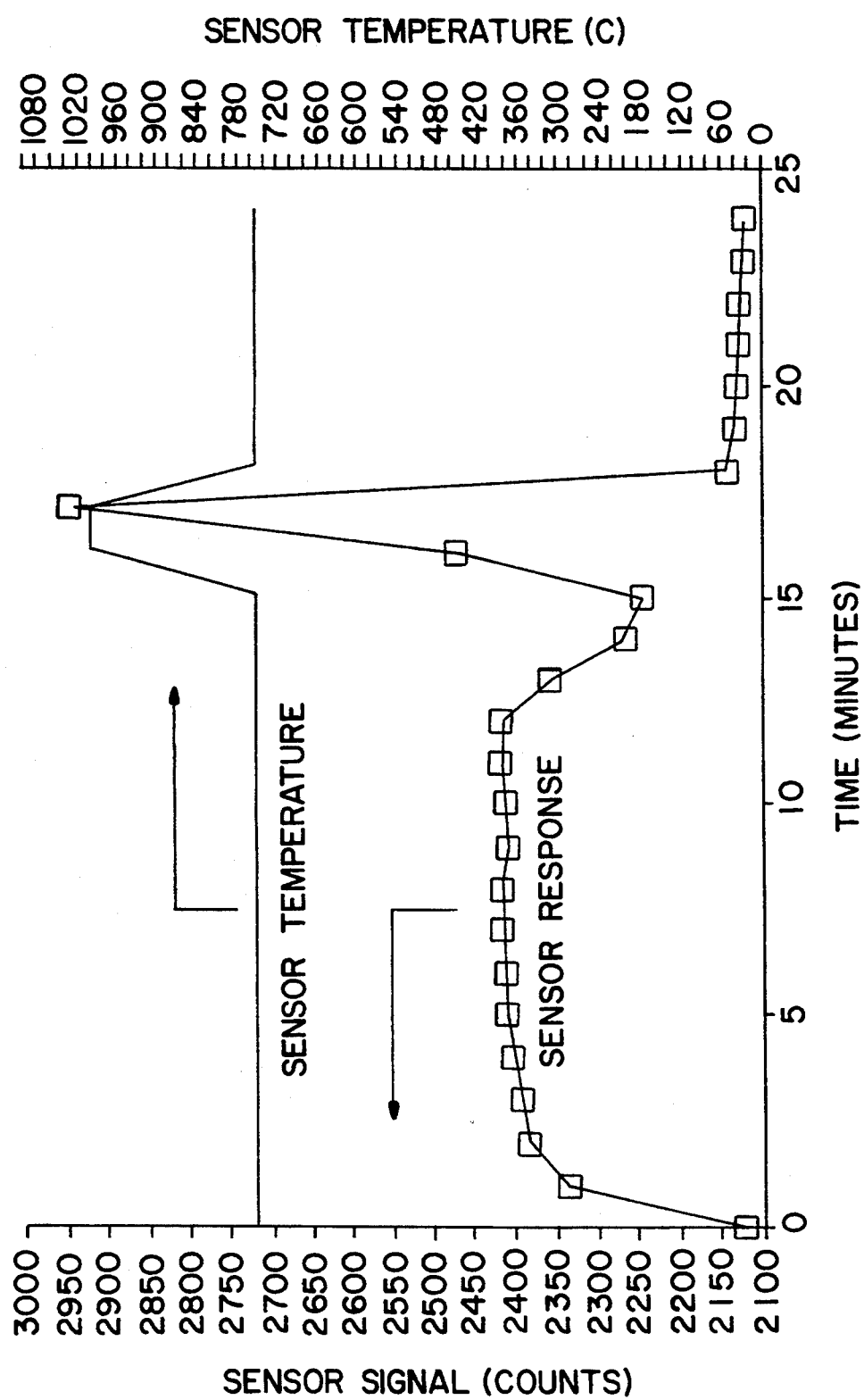
FIG. 7 shows the response and recovery of a typical sensor when exposed to a temperature cycle to speed recovery to baseline.

The effect is illustrated in the FIG. 7. Following exposure to vapor for 10 minutes (the vapor level was approximately 25 ppm), AUTOZERO is initiated. Three minutes into AUTOZERO, the sensor temperature is increased from 750 to nearly 1000° C. for 1 to 3 minutes. At the end of two minutes, the sensor temperature is adjusted back to 750° C. for the remainder of the AUTOZERO cycle.

The Main Feature of the Temperature Jump are:
1. It accelerates the recovery of the sensor to baseline.
2. Once the sensor temperature returns to 750° C., the baseline of the sensor does not change due to the Temperature Jump.
3. Temperature Jump can be (and has been) automated in the instrumentation by appropriate programming of microcomputer 42.

For a particular activated process, when the process limits recovery, the Temperature Jump is effective. Of course, to anyone skilled in the art, a Temperature Jump or cycle or alternate temperature program may be found that is also effective.

Sensor Lifetime and Stability

Without the herein disclosed improvements, a durability test demonstrated a sensor lifetime of over 20 days with continuous repetitive 10-minute exposures to a concentration of 10 ppm of carbon tetrachloride in air. The sensor response is stable over a given day, with variations of only about 10% of the signal, and is stable over the sensor lifetime, with a total variation in sensitivity of less than 50%. The lifetime appears to be a function of the exposure history of the sensor and can vary greatly from sensor to sensor. After an initial and brief burn-in, a nearly constant sensitivity was observed for over 1000 ppm-hours. The sensor was operated under constant bias. As described earlier, the lifetime may be lengthened significantly by operating the sensor with either intermittent bias or with limited exposure to high concentrations of sample.

Extending Sensor Lifetime with Multiple Bias Leads

A possible explanation of the observed shortened lifetime with increased exposure to halogenated substances is that the sensor of FIG. 1 may function as an amperometric sensor. The observed limited sensor lifetime could then be due to a build-up of a product arising from an electrochemical reaction at one sensor electrode, which can occur only at those electrode portions where the difference in potential between opposite electrodes is sufficiently high. For the configuration of FIG. 1 and circuit of FIG. 2, the potential difference between coil 14 and lead 12 may vary between 2.7 V at point 15 and 0.3 V at point 17 for a bias voltage of 3 V. Therefore, if the reaction requires a potential difference in excess of a certain value, the build-up of reaction product will occur only in the region which exceeds this value.

Figure 1B:
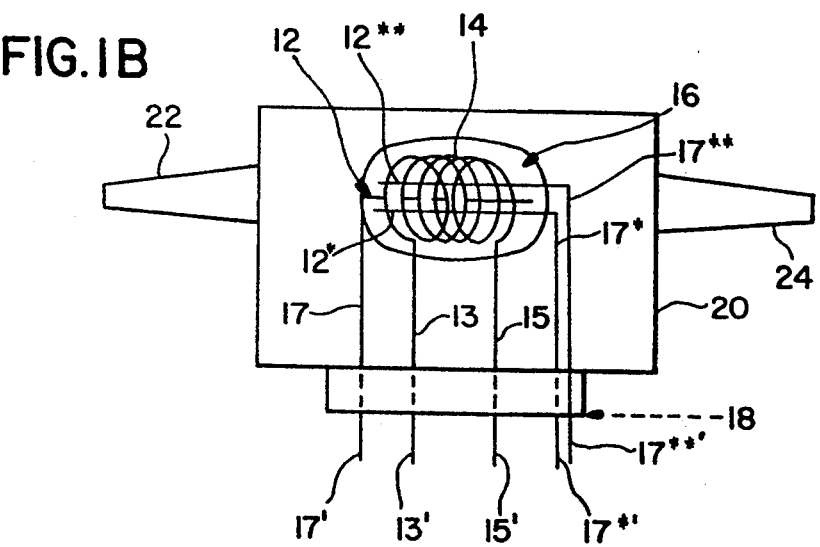
FIGS. 1B and 1C are schematic diagrams of the main components of alternative embodiments of the sensor of this invention.
Figure 1C:
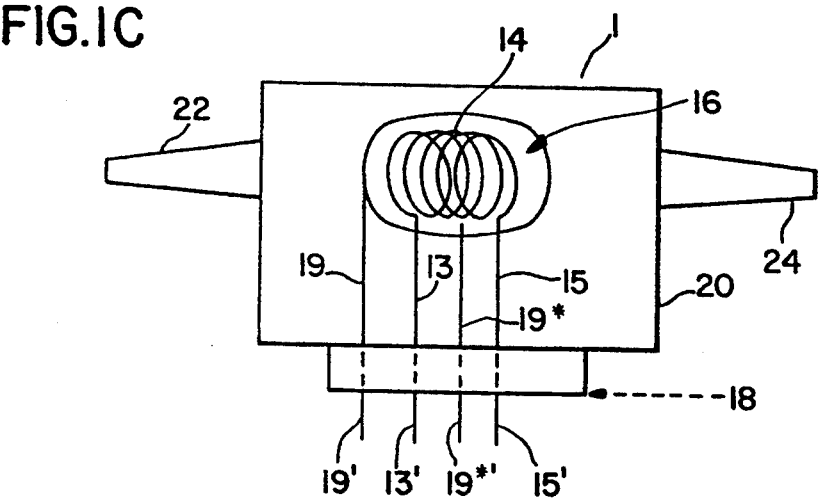

One way of alleviating this problem is to embed several sets of electrodes into the sensor and either use different sets at programmed time intervals or, when one set is used up, begin to employ the second set and then the third set of wires 12*, 12**, . . . of FIGS. 1B and 1C. This can also extend the lifetime of the sensor bead in field use. Of course, multiple (more than two) bias leads can be built into the sensor.

It also follows from this perspective that by reversing the bias at programmed time intervals, the build-up of the insulating layer should be partly diverted to a different portion of the bead, thereby extending the sensor lifetime.

In summary, the improved halogenated compounds sensor of this invention has a high sensitivity and selectivity, good precision and a prolonged lifetime. It can be used for the determination of chlorinated or brominated hydrocarbons or of HCl. Besides its obvious use as a selective sensor for the direct monitoring of halogenated compounds, it may also have possible application as a detector in gas chromatography or other instrumental analytical methods. The sensor has been used to examine a variety of chlorinated hydrocarbon vapors, including carbon tetrachloride, trichlorethylene, chloroform and 1,1,1-trichloroethane at concentrations of 0.1–500 ppm. Lower levels may be possible with a higher-gain amplifier. With its impedance-measuring circuit, the sensor is virtually insensitive to commonly occurring gases, such as $H_2O$, $N_2$, CO, $O_2$ or $NO_2$, and to halogen-free hydrocarbon vapors, such as hexane and benzene, yet it can detect combustible compounds with its power-measuring circuit. The sensor is quite stable over its entire lifetime and is not affected by humidity or by the presence of air.

Although the afore-disclosed improvements have been addressed primarily to a halogenated compounds sensor, it will be clear to those skilled in the art that other solid-state chemical sensors, especially those whose performance and lifetime may be adversely affected by the build-up of an insulating reaction product, may also benefit from similar modifications in composition, structure, techniques, and associated apparatus. Examples of said other solid-state sensors may be those comprising various formulations of lanthanum fluoride silicate for the detection of halogenated compounds, as disclosed in U.S. Pat. No. 3,751,968 of Loh and Lu, or those comprising silver compounds for the detection of sulfides or mercaptans.

There will now be obvious to those skilled in the art many modifications and variations of the afore-described embodiments. It should be possible to design tiny multiple-electrode versions of the sensor, to scale down size and cost, while improving performance, with shorter response and recovery times and improved sensitivity. By reversing the bias at programmed time intervals, it may be possible to achieve a similar effect to that of bias interruption in extending the sensor lifetime. These variations and others shall remain within the scope of the invention as defined by the following claims.

We claim:

1. In apparatus for detecting a halogenated compound comprising a solid-state sensor having two noble-metal electrodes in contact with and separated by a material comprising lanthanum fluoride silicate, wherein exposure to said substrate during operation may adversely affect the sensor lifetime, the improvement comprising a life-extending means for minimizing diverting or disturbing the buildup of solid electrically insulating reaction by product between said electrodes within the body of said sensor that results from exposure of said sensor to said compound, thereby prolonging the lifetime of said sensor.

2. The apparatus of claim 1, wherein said silicate has the chemical formula $NaLa_4(SiO_4)_3F$.

3. The apparatus of claim 1, wherein said life-extending means comprises a control means for exposing said sensor to gaseous samples and applying a voltage between said electrodes during measurement cycles and wherein said control means is programmed to apply said voltage during only a fraction of each measurement cycle.

4. The apparatus of claim 1, comprising electrical connections to said electrodes and means for switching said connections.

5. The apparatus of claim 4, wherein said control means is programmed to effect reversals of the voltage between said electrodes during successive measurement intervals.

6. The apparatus of claim 4, which comprises inclusion of additional electrodes within said material so as to form two or more alternative sets of electrodes, and wherein said control means is programmed to switch connections to said alternative sets so as to distribute the objectionable build-up throughout different parts of said material.

7. The apparatus of claim 1, wherein said life-extending means comprises electrically conductive particles interspersed within said material.

8. The apparatus of claim 7, wherein said conductive particles are metallic.

9. The apparatus of claim 7, wherein said conductive particles comprise a semiconductor.

10. The apparatus of claim 7, wherein said conductive particles comprise an ionic conductor.

11. The apparatus of claim 8, wherein said conductive particles comprise a noble metal.

12. The apparatus of claim 11, wherein said noble metal is platinum.

13. The apparatus of claim 3, wherein said life-extending means comprises a flow control means that is programmed to flow air that is depleted of said compound past said sensor during a substantial portion of each measurement cycle.

14. In apparatus for detecting a halogenated compound in a gaseous mixture comprising a sensor having two or more noble-metal electrodes in contact with and separated by a material comprising sodium lanthanum fluoride silicate, having the chemical formula $NaLa_4(SiO_4)_3F$, the improvement comprising a means for improving the sensitivity and response time of said sensor, wherein said sensitivity and response time improving means comprises solid catalytic particles interspersed within the body of said material that help convert said halogenated compound to a species that elicits an enhanced specific response from said sensor, and wherein said catalytic particles comprise an ionic salt.

15. In apparatus for detecting a halogenated compound in a gaseous mixture comprising a sensor having two or more noble-metal electrodes in contact with and separated by a material comprising sodium lanthanum fluoride silicate, and wire leads for heating the sensor to a controlled temperature, the improvement comprising a means for selective detection of both halogen-containing and combustible halogen-free compounds by the same sensor.

16. The apparatus of claim 15, wherein said selective detection means comprises a circuit means for measuring the heating power required to maintain said 17. In a method using measurement cycles to detect a halogenated compound with a solid-state sensor having two noble-metal electrodes in contact with and separated by a material comprising sodium lanthanum fluoride silicate, the improvement which comprises introducing a life-extending step for minimizing, diverting or distributing the buildup of solid electrically insulating reaction by product between said electrodes within the body of said sensor that results from exposure of said sensor to said compound, thereby prolonging the lifetime of said sensor.

18. The method of claim 17, wherein said silicate has the chemical formula $NaLa_4(SiO_4)_3F$, 19. The method of claim 17, wherein said life-extending step comprises providing a control means for applying a voltage between said electrodes and programming said control means to apply said voltage during only a fraction of each measurements cycle.

20. The method of claim 17, wherein said electrodes comprise electrical connections and said life-extending step comprises switching said connections.

21. The method of claim 20, comprising the step of effecting reversals of the voltage between said electrodes during successive measurement intervals.

22. The method of claim 17, wherein said life-extending step comprises flowing air that is depleted of said compound past said sensor during a substantial portion of each measurement cycle.

23. In a process of producing a halogenated compounds sensor having two or more noble-metal electrodes in contact with and separated by a material comprising sodium lanthanum fluoride silicate, the lifetime of said sensor being adversely affected by a buildup of solid electrically insulating reaction byproduct between said electrodes within the body of said sensor that results from exposure of said sensor to said compounds, the improvement comprising the step of modifying the structure or composition of said material so as to improve the lifetime of said sensor, which comprises the step of introducing additional constituents within said material.

24. The process of claim 23, wherein said additional constituents comprise two or more additional sets of electrodes.

25. The process of claim 23, wherein said constituents comprise said electrically conductive or catalytic particles interspersed within the body of said material.

26. The process of claim 25, wherein said particles are metallic.

27. The process of claim 25, wherein said particles comprise a semiconductor.

28. The process of claim 25, wherein said particles comprise an ionic conductor.

29. The process of claim 25, wherein said particles comprise a noble metal.

30. The process of claim 29, wherein said noble metal is platinum.

31. In a process of producing a halogenated compounds sensor having two or more noble-metal electrodes in contact with and separated by a material comprising sodium lanthanum fluoride silicate, the improvement comprising the step of modifying the physical structure or properties of said material so as to improve the lifetime, sensitivity or response characteristics of said sensor, wherein said structural modification comprises increasing the intrinsic porosity of said material.

32. In a method for detecting a halogenated compound in a gaseous mixture using a sensor having two or more noble-metal electrodes in contact with and separated by a material comprising sodium lanthanum fluoride silicate, and wire leads for heating the sensor to a controlled temperature, the improvement comprising selectively detecting both halogen-containing and combustible halogen-free compounds by the same sensor.

33. The method of claim 32, wherein said silicate has the chemical formula $NaLa_4(SiO_4)_3F$.

34. The method of claim 32, wherein said selective detection comprises measuring the heating power required to maintain said temperature and hence deduce the concentration of combustible analyte and independent resistive measurements to determine the concentration of chlorinated compounds.

* * * * *